United States Patent
Westacott et al.

(10) Patent No.: US 10,301,936 B2
(45) Date of Patent: May 28, 2019

(54) TIGHT GAS FORMATION PRESSURE DETERMINATION METHOD

(71) Applicant: HALLIBURTON ENERGY SERVICES, INC., Houston, TX (US)

(72) Inventors: Donald Westacott, Spring, TX (US); Luis F. Quintero, Katy, TX (US)

(73) Assignee: HALLIBURTON ENERGY SERVICE, INC., Houston, TX (US)

(*) Notice: Subject to any disclaimer, the term of this patent is extended or adjusted under 35 U.S.C. 154(b) by 254 days.

(21) Appl. No.: 15/104,508

(22) PCT Filed: Jan. 13, 2015

(86) PCT No.: PCT/US2015/011248
§ 371 (c)(1),
(2) Date: Jun. 14, 2016

(87) PCT Pub. No.: WO2015/108880
PCT Pub. Date: Jul. 23, 2015

(65) Prior Publication Data
US 2018/0163534 A1    Jun. 14, 2018

Related U.S. Application Data (60) Provisional application No. 61/930,922, filed on Jan. 23, 2014, provisional application No. 61/927,048, filed on Jan. 14, 2014.

(51) Int. Cl.
*E21B 49/06*    (2006.01)
*E21B 25/08*    (2006.01)
(Continued)

(52) U.S. Cl.
CPC .............. *E21B 49/06* (2013.01); *E21B 25/08* (2013.01); *E21B 41/005* (2013.01); *E21B 43/16* (2013.01); *G01N 15/08* (2013.01); *G01N 33/241* (2013.01)

(58) Field of Classification Search
CPC ....... E21B 49/06; G01N 15/08; G01N 33/241
See application file for complete search history.

(56) References Cited

U.S. PATENT DOCUMENTS 3,646,997 A * 3/1972 Chenevert ................ C09K 8/32
166/254.2
3,664,426 A * 5/1972 Chenevert ............... E21B 43/26
166/308.1
(Continued)

FOREIGN PATENT DOCUMENTS

| CN | 102220865 | 4/2014 |
|---|---|---|
| WO | 2011/133885 | 10/2011 |

(Continued)

OTHER PUBLICATIONS

PCT International Search Report and Written Opinion, dated Apr. 29, 2015, Appl No. PCT/US2015/011248,"Tight Gas Formation Pressure Determination Method," Filed Jan. 13, 2015, 16 pgs.

(Continued)

*Primary Examiner* — John Fitzgerald
(74) *Attorney, Agent, or Firm* — Gilliam IP PLLC (57) ABSTRACT

A disclosed pressure determination method for tight gas formations includes: obtaining a downhole core sample of a tight gas formation penetrated by a borehole, the core sample having been sealed in a pressure-maintaining core vault during transport out of the borehole; determining an effective pore space of the core sample; deriving the number of moles of gas retrieved with the core sample; and combining the effective pore space and the number of moles together with a downhole temperature to get an estimated formation pressure. A system embodiment includes: a core vault that provides pressure-preserved transport of a core sample from a tight gas formation; a collection chamber that attaches to the core vault to measure volumes of liquid and gas fluids from the core sample; and a processing unit that (Continued)

determines an estimated formation pressure based on said volumes, a downhole temperature, and an effective pore space of the core sample.

14 Claims, 8 Drawing Sheets

(51) Int. Cl.
  G01N 15/08 (2006.01)
  G01N 33/24 (2006.01)
  E21B 41/00 (2006.01)
  E21B 43/16 (2006.01)

(56) References Cited

U.S. PATENT DOCUMENTS

| | | | | |
|---|---|---|---|---|
| 3,702,564 A * | 11/1972 | Chenevert | ............... | C09K 8/36 |
| | | | | 73/152.11 |
| 4,627,270 A * | 12/1986 | Jones | ............... | G01N 15/088 |
| | | | | 73/38 |
| 5,263,360 A * | 11/1993 | Blauch | ............... | C09K 8/58 |
| | | | | 166/250.02 |
| 5,265,462 A | 11/1993 | Blauch et al. | | |
| 5,275,063 A * | 1/1994 | Steiger | ............... | G01N 33/241 |
| | | | | 73/865.6 |
| 5,297,420 A * | 3/1994 | Gilliland | ............... | G01N 15/08 |
| | | | | 73/38 |
| 6,247,358 B1 * | 6/2001 | dos Santos | ............... | E21B 25/08 |
| | | | | 166/282 |
| 8,307,704 B2 * | 11/2012 | Georgi | ............... | G01V 9/00 |
| | | | | 73/152.07 |
| 8,857,243 B2 * | 10/2014 | Valenza, II | ............... | G01N 15/088 |
| | | | | 73/38 |
| 8,920,029 B2 * | 12/2014 | Maucec | ............... | G01N 33/24 |
| | | | | 378/208 |
| 9,709,477 B2 * | 7/2017 | Chertov | ............... | G01N 15/082 |
| 9,709,478 B2 * | 7/2017 | Chertov | ............... | G01N 15/082 |
| 9,746,410 B2 * | 8/2017 | Chertov | ............... | G01N 15/082 |
| 9,816,376 B2 * | 11/2017 | Pope | ............... | E21B 49/088 |
| 9,927,344 B2 * | 3/2018 | Chertov | ............... | G01N 15/082 |
| 2010/0161229 A1 | 6/2010 | Georgi et al. | | |
| 2012/0152548 A1 | 6/2012 | Hinkel et al. | | |
| 2014/0021345 A1 * | 1/2014 | Maucec | ............... | G01N 33/24 |
| | | | | 250/260 |
| 2014/0300895 A1 * | 10/2014 | Pope | ............... | E21B 47/102 |
| | | | | 356/301 |
| 2015/0362419 A1 * | 12/2015 | Chertov | ............... | G01N 15/088 |
| | | | | 73/38 |
| 2015/0369718 A1 * | 12/2015 | Chertov | ............... | G01N 15/088 |
| | | | | 73/38 |
| 2015/0369719 A1 * | 12/2015 | Chertov | ............... | G01N 15/088 |
| | | | | 73/38 |
| 2016/0041079 A1 * | 2/2016 | Chertov | ............... | G01N 15/088 |
| | | | | 73/38 |

FOREIGN PATENT DOCUMENTS

| | | |
|---|---|---|
| WO | 2015/108880 | 7/2015 |
| WO | 2015/108884 | 7/2015 |

OTHER PUBLICATIONS

PCT International Search Report and Written Opinion, dated Appl No. PCT/US2015/011255,"Effective Porosity Determination for Tight Gas Formations," Filed Jan. 13, 2015, 14 pgs.

Espinal, Laura, "Porosity and its Measurement", Characterization of Materials, edited by Elton N. Kaufmann, Copyright 2012 John Wiley & Sons, Inc., 9 pgs.

* cited by examiner

TIGHT GAS FORMATION PRESSURE DETERMINATION METHOD

CROSS-REFERENCE TO RELATED APPLICATIONS

The present application claims priority to U.S. Pat. App. 61/927,048, titled "Tight Gas Formation Pressure Determination Method", filed Jan. 14, 2014 by inventors Donald Westacott and Luis F. Quintero, and further claims priority to U.S. Pat. App. 61/930,922, titled "Effective Porosity Determination for Tight Gas Formations", filed Jan. 23, 2014 by inventors Luis F. Quintero and Donald Westacott. Each of these applications is hereby incorporated herein by reference.

BACKGROUND

An important factor for managing the development and production of hydrocarbons from a reservoir is the reservoir pressure. The most common practice for determining reservoir pressure relies on pressure transient analysis (PTA) of the buildup or drawdown responses to a change in borehole conditions. However, when applied to tight gas formations, PTA methods can be inaccurate and unreliable. Fundamentally, such methods presume a measurable dynamic response, whereas the low permeability of a typical virgin tight gas formation yields insufficient gas flow for a meaningful dynamic measurement.

Another existing approach, known as rate transient analysis (RTA) or dynamic data analysis (DDA), attempts to address this issue by applying the fundamental flow-pressure relationships to a much larger data set, i.e., the production data. These methods match the production curves (including responses to changing borehole conditions) to type curves for pre-existing reservoir models. While these methods are more robust for tight gas formations than PTA, they unfortunately require a substantial amount of time to collect enough data points.

BRIEF DESCRIPTION OF THE DRAWINGS

Accordingly, there are disclosed in the drawings and detailed description specific embodiments of a tight gas formation pressure determination method. In the drawings.

It should be understood, however, that the specific embodiments given in the drawings and detailed description do not limit the disclosure. On the contrary, they provide the foundation for one of ordinary skill to discern the alternative forms, equivalents, and modifications that are encompassed in the scope of the appended claims.

DETAILED DESCRIPTION

The following disclosure provides for a novel method, apparatus, and system for determining reservoir pressure ($P_{Res}$) in gas-bearing tight formations through analysis at surface/lab conditions of pressure-preserved downhole core samples. The disclosed approach employs measurements of downhole temperature and the fundamental gas laws, $P_1V_1T_2 = P_2V_2T_1$; $PV = ZnRT$, together with mixing laws for density of fluids, to calculate the original $P_{Res}$ in a gas-bearing tight formation.

Throughout the text, the suffix "o" denotes original conditions, "1" denotes coring conditions, and "2" denotes lab conditions. Primed subscripts 2' and 2" may be used to refer to different components of a quantity under lab conditions (e.g., different portions of a volume). References to effective porosity $\phi_e$ include both inter-grain and intra-grain porosity of the core sample. When multiplied by the volume of the core sample, the effective porosity provides the effective pore volume (also known as the "effective pore space") of the core sample.

Fundamental Concepts.

Reservoir conditions in a dry gas reservoir are such that the fluid is outside of the P-T envelope, and hence exist in a single phase. The reservoir temperature is above the cricondentherm (maximum temperature above which liquid cannot be formed regardless of pressure). Hence the fluid can only be in a gaseous phase.

Figure 1A:
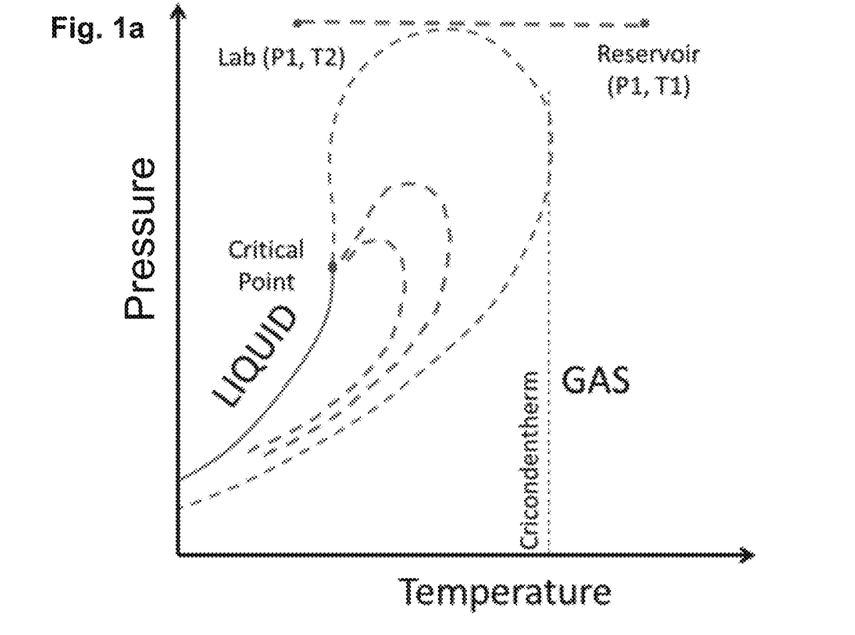
FIGS. 1a-1c are illustrative P-T diagrams of a dry gas, respectively showing paths taken by a pressure-preserved core, a conventional core, and a pressure-preserved core after releasing the pressure.
Figure 1B:
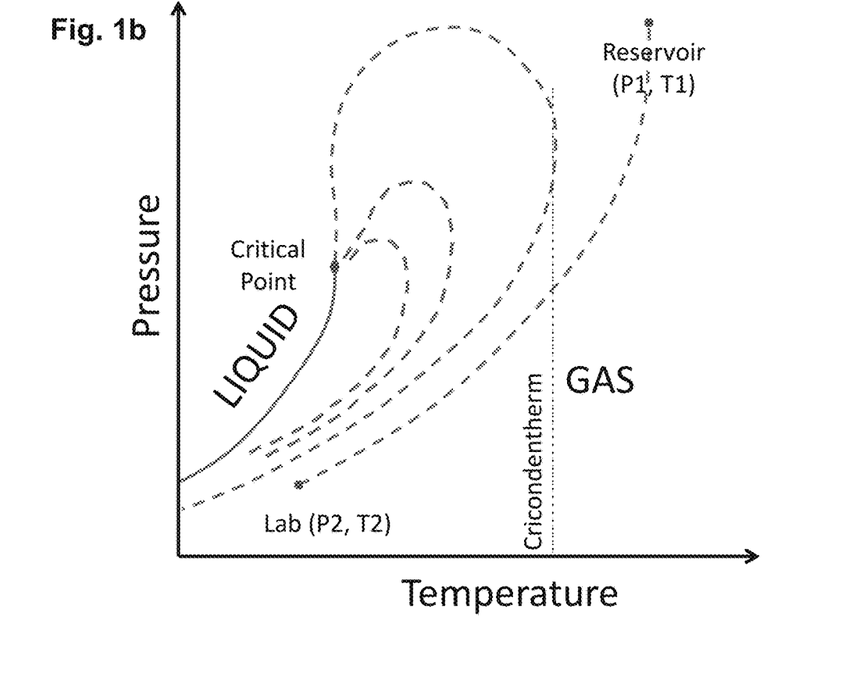

In the absence of liquids and with a rock of zero compressibility, gas trapped in a pressure-preserved core sample when brought from the reservoir to surface will only experience a change in temperature, as shown in FIG. 1a. In this scenario, all gas molecules are recovered in the core sample. For comparison, gas recovered in a conventional core sample will have followed a path as shown in FIG. 1b, typically with the core sample losing gas molecules en route to the surface.

Drilling and Coring: Hydrodynamics.

Figure 2A:
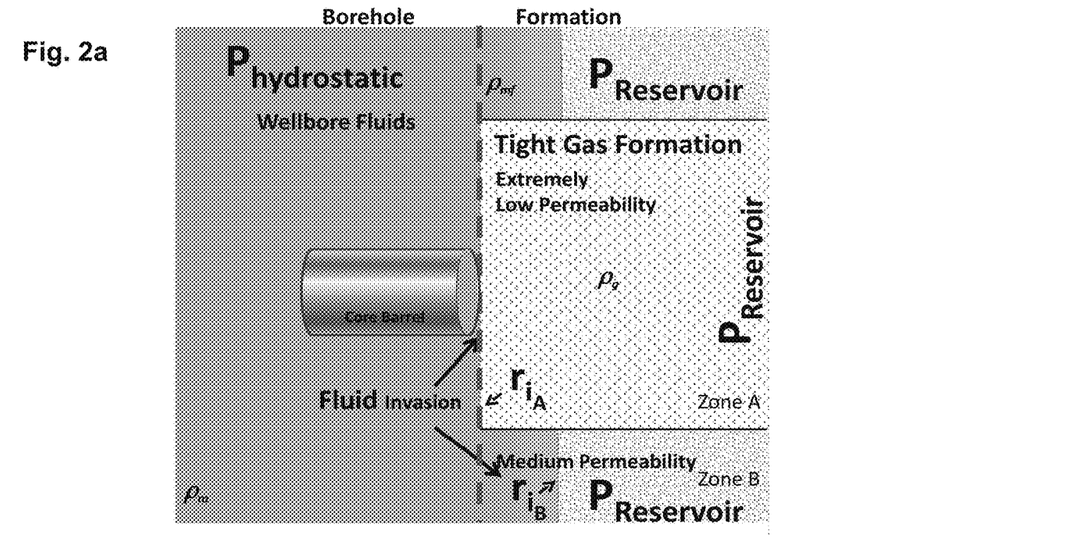
FIGS. 2a-2b are schematic pressure distribution maps before and after an illustrative coring operation.
Figure 2B:
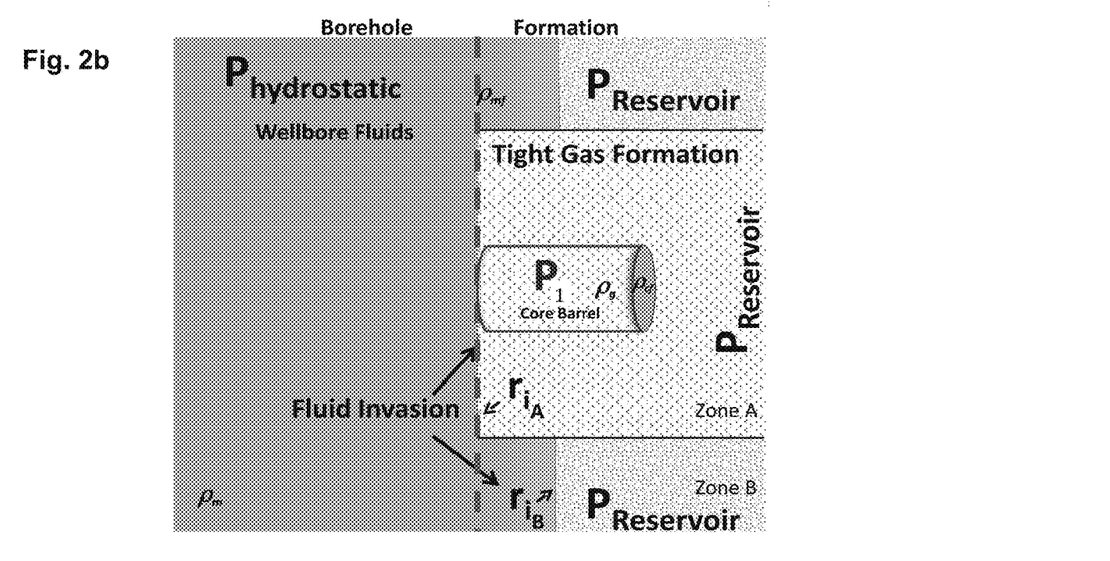

While drilling conventional formations, wellbore fluids (of density $\rho_m$) exert a hydrostatic pressure ($P_{hyd}$) which is greater than the reservoir pressure ($P_{Res}$), and hence mud filtrate (of density $\rho_{mf}$) invades the formation up to a radius of invasion ($r_i$) as shown in FIG. 2a. (In FIGS. 2a and 2b, the radius of invasion for Zone A is labeled $r_{iA}$ and the radius of invasion for Zone B is labeled $r_{iB}$.) Mud additives quickly create a pseudo-impermeable layer (mudcake) that prevents the filtration process from continuing indefinitely. Hence the formation effective porosity ($\phi_e$) determines the maximum extent of the radius of invasion for low to high permeable formations. On a short time scale (the instantaneous or spurt-invasion process), it is the formation permeability (k) that controls the radius of invasion. In a tight gas formation where permeabilities are in the order of micro- and nano-darcies, the invasion is extremely shallow, on the order of minute fractions of an inch.

Similar fluid dynamics occur during coring operations, where a hollow coring bit cuts a cylindrical core sample from the side or bottom of a borehole. As the barrel of the coring bit presses a circle of cutting teeth against the formation to cut a circular trench around the core sample, the mud present in the borehole provides lubrication, but also transmits the hydrostatic pressure $P_{hyd}$ to the formation being exposed by the barrel of the coring bit while coring. In many cases this would tend to displace gas (of density $\rho_g$) deeper into the formation. However, since this disclosure deals with formations of extremely low permeability and the coring process is in the order of minutes, the radius of invasion in the core sample is negligible. In other words, the mud filtrates only cover ("paint") the core sample without penetrating into it (see FIG. 2b). With the above assumptions it is clear that the combination of extremely low permeability and the short time required for the coring do not allow gas to be displaced from the core sample.

Once the circular trench around the core sample has been cut to the desired depth (which is the desired length of the core sample), the core sample is separated from the formation, usually by rocking the bit or applying a sudden acceleration transverse to the axis of the coring bit to induce a shear fracture near the base of the core sample. Alternatively, the bit "grabs" the base of the core sample and pulls it free from the formation. The coring bit, with the core sample still positioned in the barrel of the coring bit, is then retracted from the formation.

Figure 3:
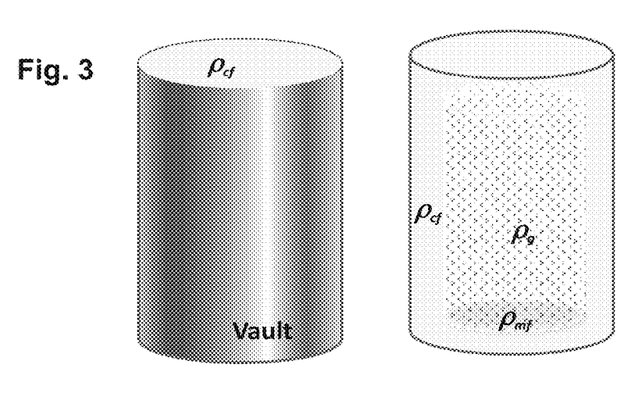
FIG. 3 shows schematic material distribution maps before and after an illustrative coring operation.

Conventional coring tool designs retrieve the coring tool to the surface with the core sample still held in the barrel of the coring bit. Some coring tool embodiments, however, displace the core sample from the barrel of the coring bit into a core vault and seal the core vault to prevent the escape of any fluids or gases as the coring tool is retrieved to the surface. In particular, certain contemplated coring tool embodiments actively preserve the pressure inside the vault as the coring tool is retrieved to the surface, even as the tool undergoes a temperature decrease during transport. Such core samples are referred to herein as "pressure preserved core samples". In at least some coring tool embodiments, the core vault is initially filled with a high density coring fluid, $\rho_{cf}$ (e.g. sodium bromide). Once the tool has placed the core sample in the core vault and sealed the vault, the volume of all fluids trapped in the core vault ($V_f$) will be a mix of mud filtrate, coring fluid, irreducible water, and gas (See FIG. 3).

Since gas can only be trapped within the effective porosity of the core sample, $\phi_e$, then the total volume of producible fluids $V_f$ in the core vault is the volume of gas, plus the volume of fluids that has "painted" the core sample, and the residual coring fluid $$V_f = V_{mf} + V_{cf} V_g \qquad \text{Eq. 1}$$

The total volume of the core vault is given by:

$$B = \pi r_B^2 L_B \qquad \text{Eq. 2}$$

where $r_B$ and $L_B$ refer to the internal radius and internal length of the core vault, respectively. Assuming that the effective porosity of the formation is known, via wireline logs or otherwise, and with a cylindrical core sample, the total volume of gas in the core vault is:

$$V_g = \phi_e C_1 \qquad \text{Eq. 3}$$

$$V_g = \phi_e \pi r_{c1}^2 L_{c1} \qquad \text{Eq. 4}$$

where $C_1$ is the volume of the core sample. In a perfectly cylindrical core sample, $$C_1 = \pi r_{c1}^2 L_{c1} \qquad \text{Eq. 5}$$

$r_{c1}$ and $L_{c1}$ refer to the radius and length of the recovered core sample, respectively, at downhole (initial) conditions. The initial volume occupied by the core sample, $C_1$, is also $$C_1 = B - V_{mf1} - V_{cf1} \qquad \text{Eq. 6}$$

and $$B = C_1 + V_{mf1} + V_{cf1} \qquad \text{Eq. 7}$$

So that the volume of gas trapped inside the core sample during coring (initial conditions) is:

$$V_{g1} = \phi_e (B - V_{mf1} V_{cf1}) \qquad \text{Eq. 8}$$

Due to $P_{hyd}$, the pressure of the core sample ($P_1$) will be slightly larger than $P_{Res}$, $$P_1 = P_{Res} + \Delta P_1 \qquad \text{Eq. 9}$$

and $$P_{Res} = P_1 - \Delta P_1 \qquad \text{Eq. 10}$$

Drilling and Coring: Thermodynamics

While drilling, wellbore fluids (at temperature $T_m$, which is measured) are in contact with the gas bearing formation which is at reservoir temperature ($T_{Res}$, assumed to be known via wireline-logs or otherwise). Although the invasion is negligible in a tight gas formation, thereby reducing heat transfer through convection, heat transfer does continue through conduction.

Figure 4A:
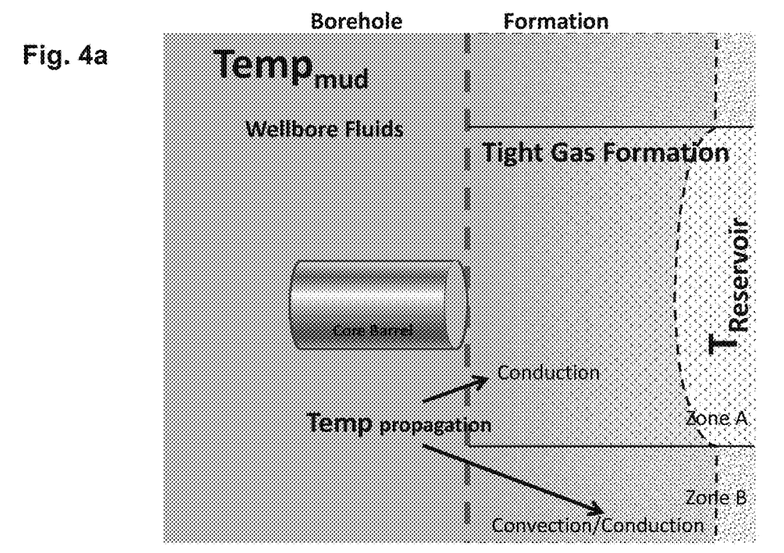
FIGS. 4a-4b are schematic temperature distribution maps before and after an illustrative coring operation.
Figure 4B:
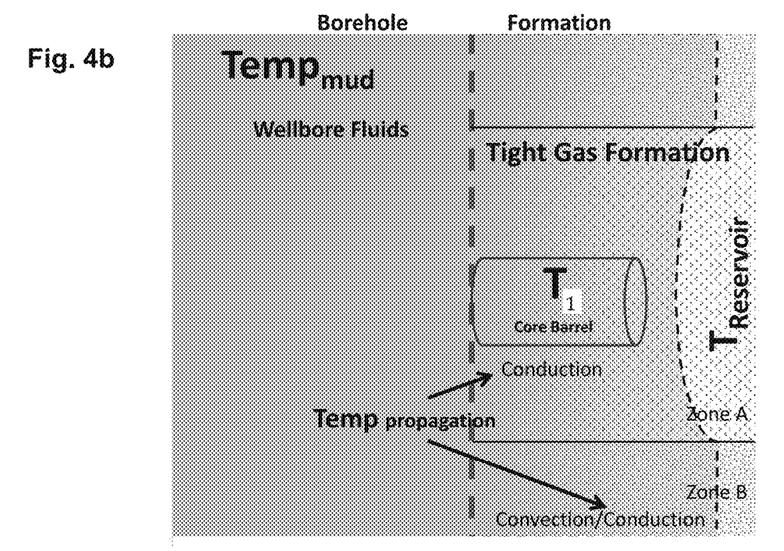

The actual temperature distribution along the wellbore while drilling will depend on several parameters, such as the temperature difference between $T_m$ and $T_{Res}$, the heat coefficient of the formation and fluids. Inside the core vault, the heat coefficient of the vault, and coring fluid will also be of importance. Nevertheless, the mass of the core vault and coring fluid are extremely small compared to the overall mass of the drilling fluid, and therefore the temperature of the core sample can be assumed to depend only on $T_m$ and $T_{Res}$. FIGS. 4a and 4b illustrate the temperature profile before and after coring.

In a pressure-preserved core sample, such as the one depicted in FIG. 4b, the temperature of the gas trapped inside the core sample ($T_1$) is bounded by $T_m$ and $T_{Res}$.

$$T_1 = T_{Res} - \Delta T_1 \qquad \text{Eq. 11}$$

Drilling and Coring: Real Gas Law

The volume of gas inside the volume of rock to be cored, before coring ($V_{go}$), follows the relationship:

$$P_{Res} V_{go} = Z_o n_o R T_{Res} \qquad \text{Eq. 12}$$

Where $Z_o$ is the gas compressibility factor at original reservoir conditions of $P_{Res}$ and $T_{Res}$, R is the universal gas constant, and n is the amount of gas (moles) in the core sample. After coring, the volume of gas trapped inside the core sample follows the same equation.

$$P_1 V_{g1} = Z_1 n_1 R T_1 \qquad \text{Eq. 13}$$

Since we are considering a very tight formation, only an infinitesimal amount of gas molecules are displaced, and hence the number of moles in the core sample remains approximately the same.

$$n_1 \approx n_o \qquad \text{Eq. 14}$$

Solving for $V_{g1}$, $$V_{g1} = \frac{z_1 n_1 R (T_{Res} - \Delta T_1)}{P_{Res} + \Delta P_1} \qquad \text{Eq. 15}$$

and $$n_1 R = \frac{\phi_e (B - V_{mf1} - V_{cf1})(P_{Res} + \Delta P_1)}{Z_i (T_{Res} - \Delta T_1)} \qquad \text{Eq. 16}$$

Releasing the Pressure

Figure 1C:
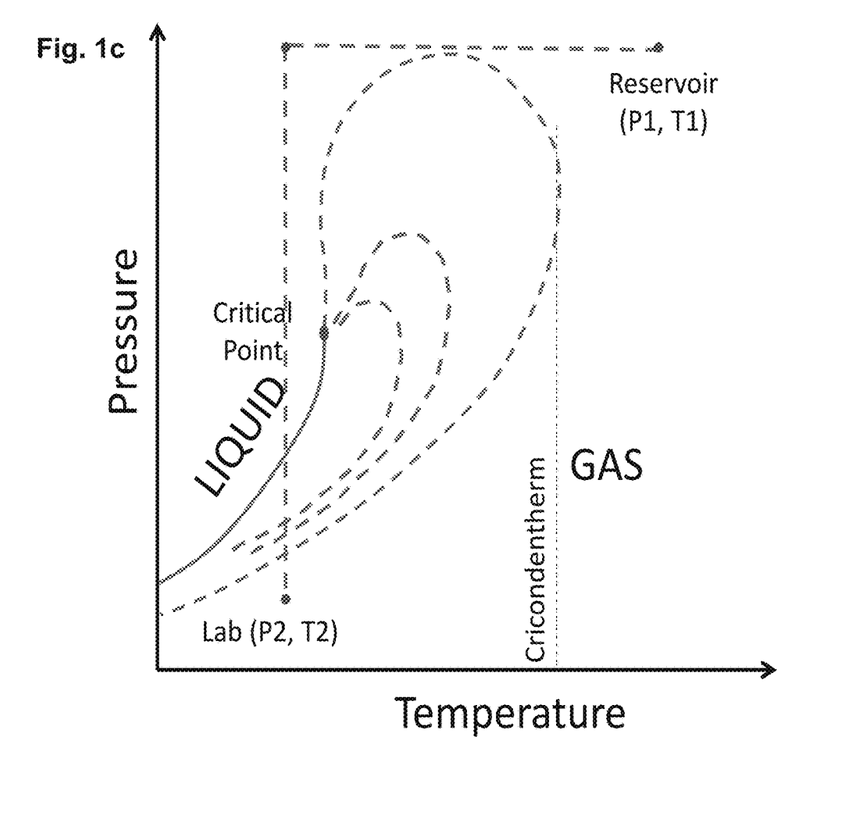
Figure 5:
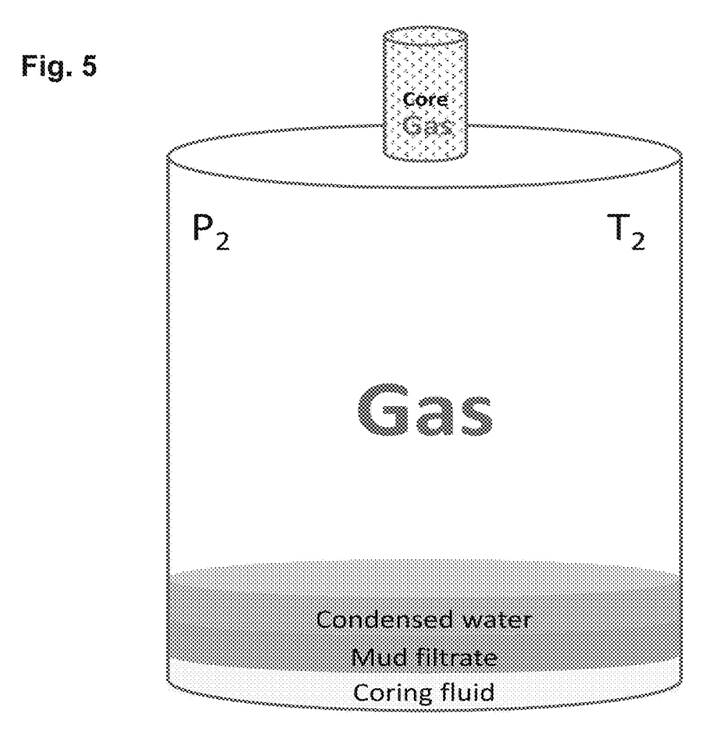
FIG. 5 is a schematic material distribution map in a collection chamber.

When the pressured preserved core sample reaches the lab, a technician attaches the core vault to a collection chamber via a sealed coupling as shown in FIG. 5. Initially, the collection chamber is filled with a vacuum or an inert gas at a known temperature and pressure. The technician releases the seal on the core vault, venting the pressure and fluids into the collection chamber. The core may be retained in the core vault as fluids drain into the collection chamber. The collection chamber has a known volume $V_2$ and, once steady state has been reached, the collection chamber provides for the measurement of pressure, temperature, and volumes for each of the fluids. As the pressure is released into the collection chamber, the fluid inside the core sample transits the path shown on FIG. 1c. Depending on lab conditions, the gas may have yielded little or no condensate, though if any condensate is present, its density can be calculated and used to determine the equivalent gas volume. Furthermore there may be some condensed water.

Therefore, the volume of fluids present in the collection chamber ($V_{f2'}$) after the pressure has been reduced to $P_2$, is given by the following expression:

$$V_{f2'} = V_{mf2} + V_{cf2} + V_w + V_{g2'} \qquad \text{Eq. 17}$$

Since the net effect of pressure and temperature changes from reservoir to lab conditions results in a net gas expansion of several orders of magnitude, it is safe to assume that all the fluids that painted the core sample have been swept out of the core sample by gas, so that the only remaining fluid in the core vault is gas, except for capillary bound water (if any).

At equilibrium, the volume of gas still trapped in the core sample ($V_{g2''}$) will be equal to the effective core space $$V_{gC} = \phi_e C_2' \qquad \text{Eq. 18}$$

where $C_2$ is the volume of the core sample under lab conditions. The core sample volume $C_2$ can be determined from physical measurements after the fluid measurements are complete and the core sample has been recovered from the core vault. Due to the change in pressure and temperature, the core sample volume $C_2$ may be different than the initial core sample volume downhole $C_1$. If desired, the compressibility and temperature coefficient of the core sample can be measured and used to estimate the downhole core sample volume $C_1$.

After the connection of the core vault to the collection chamber, the total volume of fluids at lab conditions s also given by the volume of the chamber ($V_{ch}$) plus the empty space in the core vault (core vault minus the volume of the core sample) which is now occupied by gas ($V_{gB}$), plus the effective pore space of the core sample, $$V_{f2} = V_{ch} + (B - C_2) + \phi_e C_2 \qquad \text{Eq. 19}$$

The total volume of gas in the collecting chamber, $V_{gch}$, is $$V_{gch} = V_{ch} - V_{mf2} - V_{cf2} - V_w \qquad \text{Eq. 20}$$

The total volume of gas at lab conditions, $V_{g2}$, is:

$$V_{g2} = V_{gC} + V_{gch} + V_{gB}$$

And therefore, $$V_{g2} = V_{ch} - V_{mf2} - V_{cf2} - V_w + (B - C_2) + \phi_e C_2 \qquad \text{Eq. 21}$$

Since $$V_{g2} = \frac{Z_2 n_2 R(T_2)}{P_2} \qquad \text{Eq. 22}$$

$$n_2 R = \left[\frac{V_{ch} - V_{mf2} - V_{cf2} - V_w + (B - C_2) + \phi_e C_2}{Z_2 T_2}\right] P_2 \qquad \text{Eq. 23}$$

which represents the number of moles of gas in the lab.

Since the coring tool employed a sealed core vault to transport the pressure-preserved core sample, the number of moles in the lab and during coring is the same.

$$n_2 = n_1 \qquad \text{Eq. 24}$$

Using the mud filtrate ($C_{mf}$) and coring fluid ($c_{cf}$) compressibilities $$V_{mf1} = V_{mf2}[1 - c_{mf}(P_2 - P_1)] \qquad \text{Eq. 25}$$

and $$V_{cf1} = V_{cf2}[1 - c_{cf}(P_2 - P_1)] \qquad \text{Eq. 26}$$

Recalling Eq. 16, $$\frac{\phi_e\{B - V_{mf1} - V_{cf1}\} P_1}{Z_1 T_1} = \qquad \text{Eq. 27}$$

$$\left[\frac{V_{ch} - V_{mf2} - V_{cf2} - V_w + (B - C_2) + \phi_e C_2}{Z_2 T_2}\right] P_2$$

$$P_1 = \left[\frac{V_{ch} - V_{mf2} - V_{cf2} - V_w + (B - C_2) + \phi_e C_2}{Z_2 T_2}\right] \frac{P_2 Z_1 T_1}{\phi_e\{B - V_{mf1} - V_{cf1}\}} \qquad \text{Eq. 28}$$

Equation 28 should be solved iteratively, since $$Z_1 = f(P_1) \qquad \text{Eq 29}$$

$$V_{mf1} = f(P_1) \qquad \text{Eq 30}$$

$$V_{cf1} = f(P_1) \qquad \text{Eq 31}$$

Measurements

The following parameters can be measured with extreme accuracy at the lab: $V_{ch}$, $V_{mf2}$, $V_{cf2}$, $V_w$, B, $P_2$ and $T_2$, $T_m$ and $P_{hyd}$ can be measured downhole. $\varphi_e$ can be estimated downhole via wireline logs, or in the lab. A very good approximation of $C_2$ ($C_{2th}$) can be measured or calculated. The compressibilities $c_{cf}$ and $c_{mf}$ can also be determined. The laboratory technician can analyze the gas in the collection chamber to obtain the gas composition, molecular weight and density ($\rho_g$), so that Z=f(P.T.$\rho_g$) can be determined, and with $P_2$ and $T_2$ determine $Z_2$.

There are a number of assumptions underlying this approach.
  a) Since the permeability of the formation is very small, the time for coring is very short, core sample diameter is very small compared to the depth of the reservoir, $n_0 \approx n_1$
  b) $T_{Res}$ is known, or since the core sample is taken very close to the borehole face, $\Delta T_1 \approx 0 \rightarrow T_1 = T_m$.
  c) Since the formation is very tight, the effective porosity is the same downhole and at lab conditions.

Methodology

Figure 6:
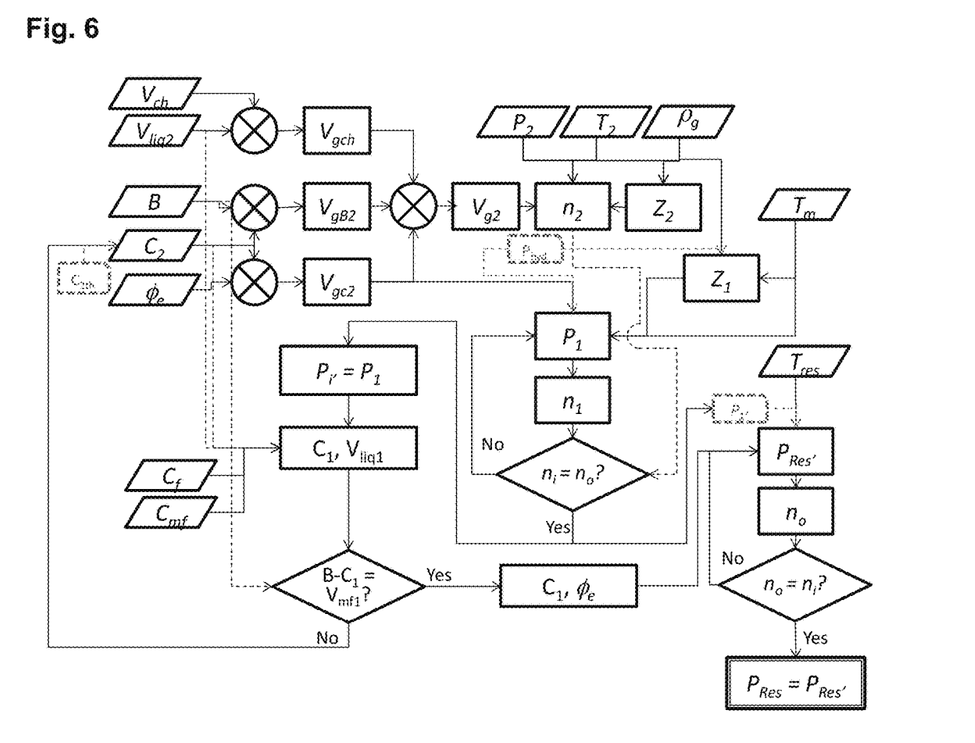
FIG. 6 is a data flow diagram of an illustrative tight gas formation pressure determination method.

FIG. 6 is a data flow diagram of an illustrative tight gas formation pressure determination method, which can be carried out with the following sequence of steps. It should be understood that the method can also be implemented with various steps performed in different order or in parallel.
  1. Obtain a pressurized core sample from a tight gas formation
  2. Keep the core sample in a vault of known volume, B 3. Obtain from wireline-logs or another source the effective porosity, $\phi_e$
4. Obtain from wireline-logs or other source the Reservoir Temperature, $T_{Res}$
5. Obtain from wireline-logs or other source the Mud Temperature during coring, $T_m$
6. Connect the Vault containing the core sample to a Collection Chamber of known volume, $V_{ch}$
7. Allow the system reach equilibrium
8. Measure the Pressure of the system at lab conditions, $P_2$
9. Measure the Temperature of the system at lab conditions, $T_2$
10. Measure the Volume of Mud Filtrate collected in the Chamber, $V_{mf2}$
11. Obtain from tables or other source the Compressibility of the Mud Filtrate, $C_{mf}$
12. Measure the Volume of Coring Fluid collected in the Chamber, $V_{cf2}$
13. Obtain from tables or other source the Compressibility of the Coring Fluid, $C_{cf}$
14. Measure the Volume of condensed Water collected in the Chamber, $V_{w2}$
15. Obtain from tables or other source the Compressibility of the condensed Water, $C_w$ (Note: from this point onwards, and for simplification purposes only, the set of three liquid volumes $V_{mf2}$, $V_{cf2}$, $V_{w2}$ will be abbreviated as $V_{liq}$)
16. With the core sample dimensions, or by other means, calculate a theoretical value of Core Sample Volume, $C_{2th}$
17. Make the Core Sample Volume at lab conditions, $C_2$ equal to $C_{2th}$
18. Calculate the Volume of gas in the empty space of the vault, $V_{gB}$
19. Calculate the Volume of gas in the collection Chamber, $V_{gch}$
20. Calculate the Volume of gas in the core sample, $V_{gC2}$
21. Add $V_{gB}$, $V_{gch}$, and $V_{gC}$ to obtain the total volume of gas at lab conditions, $V_{g2}$
22. Obtain through measurements or other source, the gas molecular weight or density, $\rho_g$
23. Obtain from correlations, tables or other source, the gas compressibility factor as a function of pressure, temperature and gas density, $Z=f(P,T,\rho_g)$
24. Using $P_2$, $T_2$ and $\rho_g$, calculate with $Z=f(P,T,\rho_g)$ or obtain through other methods, the gas compressibility factor at lab conditions, $Z_2$
25. Calculate using equation 23 or other method, the number of moles of gas corresponding, to the lab volume of gas, $n_2$
26. Obtain from wireline-logs or other method the hydrostatic pressure of the wellbore while coring, $P_{hyd}$
27. Make the core sample pressure while coring, $P_1$ equal to $P_{hyd}$
28. Using $P_1$, $T_m$ and $\rho_g$, calculate with $Z=f(P, T, \rho_g)$ or obtain through other methods, the gas compressibility factor at coring conditions, $Z_1$
29. With the volume of gas in the core sample at lab conditions, $V_{gC2}$, $P_1$, $T_m$ and $Z_1$, calculate using equation 10 the number of gas moles in the core sample during coring, $n_1$
30. Compare $n_1$ with $n_2$. If they are not equal, select a new value of $P_1$, and repeat steps 28 to 30 until the match is achieved. (Iteration 1)
31. Make a temporary value of $P_i'$ equal to $P_1$
32. Obtain from tables of other source the Compressibility of the core sample material, $C_f$
33. With $C_f$, $C_2$, $P_2$ and $P_i$, Calculate the volume of the Core sample at coring conditions, $C_1$
34. With $C_{liq}$, $V_{liq}$, $P_2$ and $P_i$. Calculate the volume of the liquids trapped in the vault at coring conditions,
35. Verify that the volume of liquids at coring conditions $V_{liq1}$ is identical to the difference between the vault volume, B, and the Core sample volume at coring conditions, $C_1$. If they are not equal, select a new value of $C_2$, and repeat steps 18 to 35 until the match is achieved (Iteration 2).
36. Multiply $C_1$ and $\phi_e$ to obtain the volume of gas in the core sample at coring conditions, $V_{gC1}$
37. The pressure in the core sample during coring has been obtained, $P_i = P_i$.
38. Make a temporary value of Reservoir Pressure equal to the pressure during coring, $P_{Res'} = P_i$
39. Using $P_{Res'}$, $T_{res}$ and $\rho_g$, calculate with $Z=f(P, T, \rho_g)$ or obtain through other methods, the gas compressibility factor at reservoir conditions, $Z_o$
40. With $V_{gC1}$, $P_1$, $T_m$ and $Z_1$, calculate using equation 12 the number of gas moles in the core sample at reservoir conditions, $n_o$
41. Compare $n_o$ with $n_1$. If they are not equal, select a new value of $P_{Res'}$, and repeat steps 39 to 41 until the match is achieved. (Iteration 3).
42. The reservoir pressure in the core sample during coring has been obtained, $P_{Res} = P_{Res'}$.

The disclosed method enables the determination of an estimated formation pressure $P_{res}$ in a safe, accurate, and relatively fast way. In part, it is safe because the time require to retrieve a pressurized core sample is measured in minutes, whereas the time required to do a welltest can be days or weeks. The likelihood of a tool getting stuck downhole are therefore greatly reduced. The accuracy results from the extremely small error ranges associated with each of the input variables, particularly those measurements being made under controlled laboratory conditions as opposed to downhole. The time required for a lab calculation of the fundamental properties of Z, $V_2$, $T_2$, $P_2$, is approximately one day. The final calculation can be made in minutes with a spreadsheet. (With the use of macros, the final calculation can be performed in less than a minute.)

Figures 7, 8:
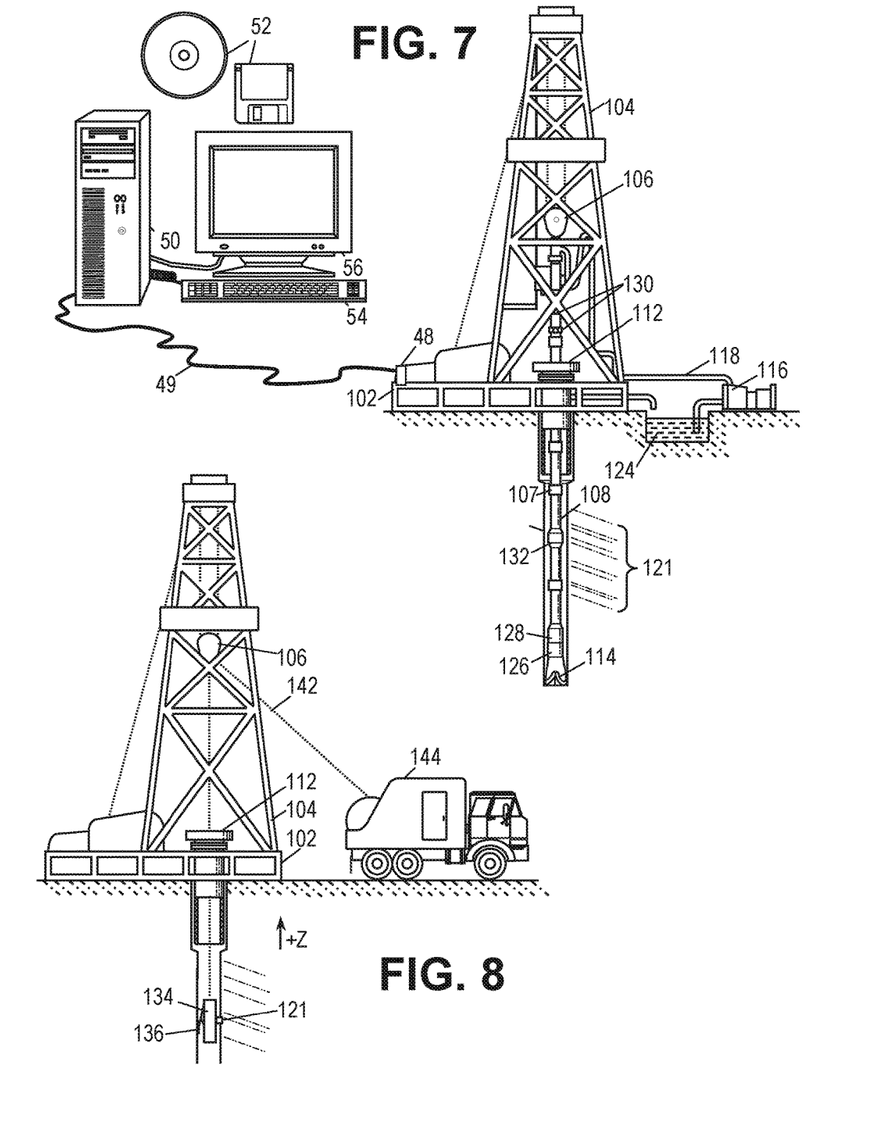
FIG. 7 is an illustrative coring while drilling environment.
FIG. 8 is an illustrative wireline coring environment.

FIG. 7 is an illustrative coring while drilling context for employing the above-disclosed principles. In the illustrated context, a drilling platform 102 is equipped with a derrick 104 that supports a hoist 106 for raising and lowering a drill string 108. The hoist 106 suspends a top drive 110 that rotates the drill string 108 as the drill string is lowered through the well head 112. The drill string 108 can be extended by temporarily anchoring the drill string at the well head 112 and using the hoist 106 to position and attach new drill pipe sections with threaded connectors 107.

Connected to the lower end of the drill string 108 is a drill bit 114. As bit 114 rotates, it creates a borehole 120 that passes through various formations 121. A pump 116 circulates drilling fluid through a supply pipe 118 to top drive 110, through the interior of drill string 108, through orifices in drill bit 114, back to the surface via the annulus around drill string 108, and into a retention pit 124. The drilling fluid transports cuttings from the borehole into the pit 124 and aids in maintaining the integrity of the borehole 120.

The drill bit 114 may be a coring bit for obtaining core samples from the bottom of the borehole. Alternatively, the bottom-hole assembly may include a sidewall coring tool 126 that can drive a coring bit into the borehole wall to obtain a core sample. The bottom hole assembly may further include one or more logging tools 128 to acquire, e.g., downhole temperature and pressure measurements, as well as a log of effective porosity of the formation. Illustrative porosity logging tools include nuclear magnetic resonance (NMR) logging tools, neutron logging tools, and acoustic logging tools, and combinations thereof. The logging tool measurements may be stored in internal memory for retrieval when the bottom hole assembly returns to the surface, or may be communicated to the surface via mud pulse telemetry or another telemetry technique. A telemetry receiver array 130 may be coupled to tubing below the top drive 110 to receive transmitted telemetry signals. Many telemetry techniques also offer the ability to transfer commands from the surface to the bottomhole assembly, thereby enabling adjustment of the tool's configuration and operating parameters.

Telemetry receiver array 130 is coupled to an interface unit 48, which demodulates and digitizes the telemetry data. A wired or wireless connection 49 enables a computer 50 to receive the measurements of downhole temperature, pressure, effective porosity, and other parameters. Software (represented in FIG. 7 by non-transient information storage media 52) configures the computer 50 to provide a user interface which interact with a user via a keyboard or other input device 54 and a monitor or other output device 56. The user can instruct the computer to retrieve and process the appropriate log parameters and combine them with the laboratory measurements outlined above to determine an initial pressure of a tight gas formation.

At various times during the drilling process, the drill string 108 is removed from the borehole as shown in FIG. 2. Once the drill string has been removed, coring operations can be conducted using a wireline tool assembly 134 suspended in the borehole by a wireline cable 142. Wireline cable 142 has conductors for transporting power to the tool and telemetry from the tool to the surface. The wireline tool assembly 134 includes one or more logging instruments and a sidewall coring tool with a leveraging arm 136 that presses the tool against the opposite borehole wall as a coring bit 121 obtains a core sample. A logging facility 144 controls the various portions of the tool assembly 134, collecting measurements from the logging instruments and initiating operation of the coring bit 121 at one or more selected positions along the borehole. Logging facility 144 includes computing facilities for processing and storing the measurements gathered by the logging instruments. Such computing facilities can apply the principles outlined herein to determine tight gas formation pressures.

Figure 9:
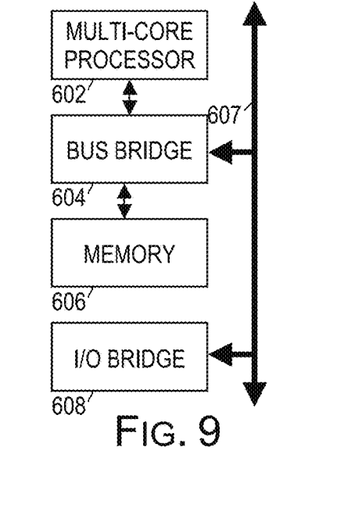
FIG. 9 is a block diagram of an illustrative pressure determination apparatus.
Figure 10:
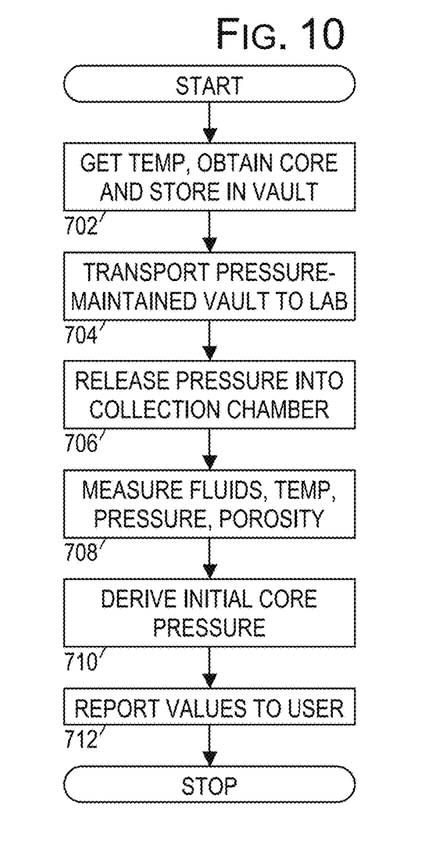
FIG. 10 is a flow chart of an illustrative pressure determination method.

Computer 50 (FIG. 7), the logging facilities 144 (FIG. 8), or some other form of processing unit can be used to carry out the formation pressure determination methods outlined by the data flow diagram of FIG. 6 or the flow chart of FIG. 10. FIG. 9 is a block diagram of one such illustrative processing unit. One or more multi-core processors 602 coordinate the operation of the unit based on software stored in memory 606 and/or in persistent storage accessible via an I/O bridge 608. A bus bridge 604 couples the processor(s) 602 and memory 606 to the rest of the system via a bus 607. Various peripherals can be coupled to the bus 607 or the I/O bridge 608, including monitors, keyboards, sound cards, data acquisition cards, and network cards. The software may include a basic operating system, spreadsheet software, and macros to carry out the disclosed methods. Alternative embodiments may employ custom software and data acquisition drivers to maximize automation of the method.

In the illustrative method embodiment of FIG. 10, the downhole tool assembly measures the borehole temperature and pressure and obtains a core sample in block 702. The tool assembly stores the core sample in a core vault or seals the barrel of the coring hit to enable the pressure-preserved transport of the sample to a surface laboratory. The tool may further measure the in-situ effective porosity of the formation. In block 704, the pressure-preserved core sample is transported to the lab. In block 706, a technician attaches the core vault or sealed coring bit barrel to an evacuated collection chamber and releases the fluids into the collection chamber. In block 708, after the collection chamber has reached steady state, the technician measures the temperature and pressure in the chamber, and further measures the volumes of the fluids (including the gas). The technician can further measure the composition of the gas and determine the compressibilities of each of the fluids, and can determine the volume of the core sample. The effective porosity of the core sample may further be determined under laboratory conditions. Based on the various measurements, in block 710 a computer determines the original formation pressure of the core sample, and in block 712 the computer reports the formation pressure to a user, e.g. by displaying it on a monitor.

It is expected that the foregoing method will enable significantly improved modeling of fracturing operations in tight dry gas and/or dry shale gas formations, leading to improved production operations. It should further enable better forecasting of ultimate recoveries in such formations.

Accordingly, embodiments disclosed herein include:

A. A tight gas formation pressure determination method that comprises: obtaining a downhole core sample of a tight gas formation penetrated by a borehole, the core sample having been sealed in a pressure-maintaining core vault during transport out of the borehole; determining an effective pore space of the core sample; deriving the number of moles of gas retrieved with the core sample; and combining the effective pore space and the number of moles together with a downhole temperature to get an estimated formation pressure.

B. A tight gas formation pressure determination system that comprises: a core vault that is sealable to provide pressure-preserved transport, the core vault receiving a core sample from a tight gas formation; a collection chamber that attaches to the core vault to receive and measure volumes of fluids and gas from the core sample; and a processing unit that, based at least in part on said volumes, a downhole temperature, and an effective pore space of the core sample, determines an estimated formation pressure.

C. A non-transient information storage medium having software that causes a processing unit carry out a tight gas formation pressure determination method comprising: obtaining a downhole temperature; determining an effective pore space of the core sample; receiving pressure, volume, and temperature measurements of a gas in a collection chamber after attachment of a core vault having a pressure-preserved core sample from a tight gas formation; calculating the number of moles of gas retrieved with the core sample; combining the effective pore space of the core sample together with the downhole temperature and the number of moles to obtain an estimated formation pressure; and displaying the estimated formation pressure.

Each of the embodiments A, B, and. C may have one or more of the following additional elements in any combination: Element 1: the determining comprises retrieving a measured porosity from a log of the tight gas formation and multiplying by a measured volume of the core sample. Element 2: the determining comprises measuring a porosity of the core sample after transport out of the borehole and multiplying by a measured volume of the core sample.

Element 3: the deriving comprises (a) connecting the core vault to a collection chamber of predetermined content and predetermined volume; and (b) measuring an equilibrium pressure and equilibrium temperature of the collection chamber after said connecting. Element 4: the known content of the collection chamber prior to connection of the core vault is a vacuum or an inert gas. Element 5: the deriving comprises (a) measuring one or more liquid volumes in the collection chamber; (b) determining a collection chamber gas volume based at least in part on the one or more liquid volumes and the predetermined volume; and (c) adding the collection chamber gas volume to the effective pore space of the core sample and a core vault space around the core sample to obtain a total gas volume. Element 6: the deriving comprises: (a) determining a gas compressibility based at least in part on a measured density or molecular weight of gas in the collection chamber; and (b) combining the compressibility with the total gas volume and equilibrium pressure and equilibrium temperature to get the number of moles of gas retrieved with the core sample. Element 7: liquid volumes are measured for each of: a mud filtrate, a coring fluid, and water. Element 8: the number of moles is estimated at least in part by: (a) receiving density or molecular weight measurements of the gas; (b) estimating a compressibility based at least in part on the density or molecular weight measurements; and (c) deriving the number of moles from the compressibility and from the pressure, volume and temperature measurements of the gas. Element 9: estimating a downhole compressibility of the gas.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A method for determining tight gas formation pressure, said method comprising:
   extracting a downhole core sample of a tight gas formation penetrated by a borehole, said extracting including sealing the core sample in a pressure-maintaining core vault during transport out of the borehole;
   measuring a porosity of the formation or the core sample;
   measuring a volume of the core sample;
   determining an effective pore space of the core sample based, at least in part, on the measured porosity and the measured volume of the core sample;
   deriving a number of moles of gas retrieved with the core sample based, at least in part, on the effective pore space;
   determining a downhole temperature; and
   determining a tight gas formation pressure based on the effective pore space, the number of moles of gas retrieved with the core sample, and the downhole temperature.

2. The method of claim 1, wherein said deriving the number of moles of gas retrieved with the core sample comprises:
   connecting the core vault to a collection chamber having known content and known volume; and
   measuring an equilibrium pressure and equilibrium temperature of the collection chamber after said connecting.

3. The method of claim 2, wherein the known content is vacuum.

4. The method of claim 2, wherein the known content is inert gas.

5. The method of claim 2, wherein said deriving the number of moles of gas retrieved with the core sample comprises:
   measuring one or more liquid volumes in the collection chamber;
   determining a collection chamber gas volume based at least in part on the one or more liquid volumes and the known volume; and
   adding the collection chamber gas volume to the effective pore space of the core sample and a core vault space around the core sample to obtain a total gas volume.

6. The method of claim 5, wherein said deriving the number of moles of gas retrieved with the core sample further comprises:
   determining a gas compressibility based at least in part on a measured density or molecular weight of gas in the collection chamber; and
   determining the number of moles of gas retrieved with the core sample based on the gas compressibility, the total gas volume, the equilibrium pressure, and the equilibrium temperature.

7. The method of claim 5, wherein said measuring one or more liquid volumes includes determining a volume and compressibility for each of: a mud filtrate, a coring fluid, and water.

8. A system for determining tight gas formation pressure, said system comprising:
   a coring device for removing a core sample from a tight gas formation;
   a core vault that is sealable to provide pressure-preserved transport, the core vault configured to receive a core sample from a tight gas formation;
   a logging tool configured to measure a downhole temperature;
   a tool to measure a porosity of the formation or the core sample;
   a collection chamber that attaches to the core vault, said collection chamber configured to receive and measure volumes of liquid and gas fluids from the core sample; and
   a processing unit configured to,
      determine an effective pore space of the core sample based, at least in part, on the measured porosity of the formation or the core sample and a measured volume of the core sample; and
      determine a tight gas formation pressure based, at least in part, on said volumes of liquid and gas fluids, the measured downhole temperature, and the effective pore space of the core sample.

9. The system of claim 8, wherein the processing unit determines the effective pore space by retrieving a measured porosity from a log of the tight gas formation and multiplying by the measured volume of the core sample.

10. The system of claim 8, wherein as part of determining the formation pressure, the processing unit determines a number of moles of gas retrieved from the core sample by, in part, obtaining an equilibrium temperature and equilibrium pressure of the collection chamber after the attachment of the collection chamber to the core vault.

11. The system of claim 10, wherein as part of determining the formation pressure, the processing unit further obtains a gas compressibility based at least in part on a measured density or molecular weight of gas in the collection chamber.

12. The system of claim 11, wherein the processing unit combines the gas compressibility with equilibrium temperature, equilibrium pressure, and total gas volume to determine a number of moles of gas retrieved with the core sample.

13. The system of claim 12, wherein the processing unit calculates the formation pressure based on the number of moles of gas, the effective pore space, the downhole temperature, and an estimated downhole gas compressibility.

14. The system of claim 12, wherein the processing unit calculates the total gas volume by adding a measured collection chamber gas volume to the effective pore space of the core sample and to a core vault space around the core sample.

* * * * *